(12) United States Patent
Radney

(10) Patent No.: US 7,296,575 B1
(45) Date of Patent: Nov. 20, 2007

(54) HEADGEAR AND INTERFACE ASSEMBLY USING SAME

(75) Inventor: Steven B Radney, Pittsburgh, PA (US)

(73) Assignee: RIC Investments, LLC, Wilmington, DE (US)

( * ) Notice: Subject to any disclaimer, the term of this patent is extended or adjusted under 35 U.S.C. 154(b) by 87 days.

(21) Appl. No.: 10/993,049

(22) Filed: Nov. 19, 2004

Related U.S. Application Data

(60) Provisional application No. 60/527,235, filed on Dec. 5, 2003.

(51) Int. Cl.
    A62B 18/08 (2006.01)

(52) U.S. Cl. ............... 128/207.11; 128/207.13; 128/207.17

(58) Field of Classification Search .......... 128/206.11, 128/206.12, 206.13, 206.18, 206.21, 207.11, 128/207.13, 207.17, 207.18, DIG. 26; 2/448; 351/43
See application file for complete search history.

(56) References Cited

U.S. PATENT DOCUMENTS

| 911,476 | A | * | 2/1909 | Cheesman | 128/206.12 |
| 2,047,216 | A | | 7/1936 | McKesson | |
| 5,517,986 | A | | 5/1996 | Starr et al. | |
| 5,724,965 | A | * | 3/1998 | Handke et al. | 128/207.13 |
| 5,964,218 | A | * | 10/1999 | Smith et al. | 128/201.25 |
| 6,044,844 | A | | 4/2000 | Kwok et al. | |
| 6,104,824 | A | * | 8/2000 | Ito | 381/381 |
| 6,119,694 | A | * | 9/2000 | Correa et al. | 128/207.13 |
| 6,252,970 | B1 | | 6/2001 | Poon et al. | |
| 6,325,507 | B1 | | 12/2001 | Jannard et al. | |
| 6,470,886 | B1 | * | 10/2002 | Jestrabek-Hart | 128/207.13 |
| 6,494,207 | B1 | | 12/2002 | Kwok | |
| 6,497,232 | B2 | * | 12/2002 | Fecteau et al. | 128/207.11 |
| 6,732,733 | B1 | * | 5/2004 | Brostrom et al. | 128/206.27 |
| 6,745,404 | B2 | * | 6/2004 | Chen-Lieh | 2/428 |

OTHER PUBLICATIONS

Respironics, Inc., Simpicity™ Headgear, 2002, Respironics, Inc.
RESMED, Mirage Vista™ Mask, 2002, ResMed Ltd.

* cited by examiner

Primary Examiner—Steven O. Douglas
(74) Attorney, Agent, or Firm—Michael W. Haas

(57) ABSTRACT

A headgear for attaching an object to a head of a user that is defined by a support beam and first and second ear loops coupled to opposite ends of the beam. The support beam generally wraps around a back of a user's neck or head and remains below the external occipital protuberance at all times during use of the headgear. This configuration minimizes the contact between the portions of the headgear and the user's hair. The first and second ear loops each include an upper arm adapted to be positioned above the ear, a lower arm adapted to be positioned below the ear, or both. An interface device is coupled to the headgear and held on the user's head by a tensioning force pulling the interface device toward the user.

32 Claims, 7 Drawing Sheets

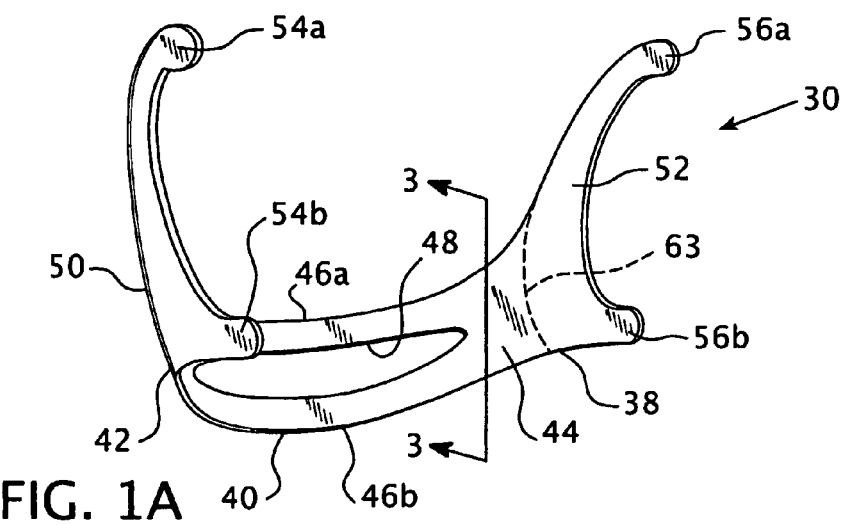
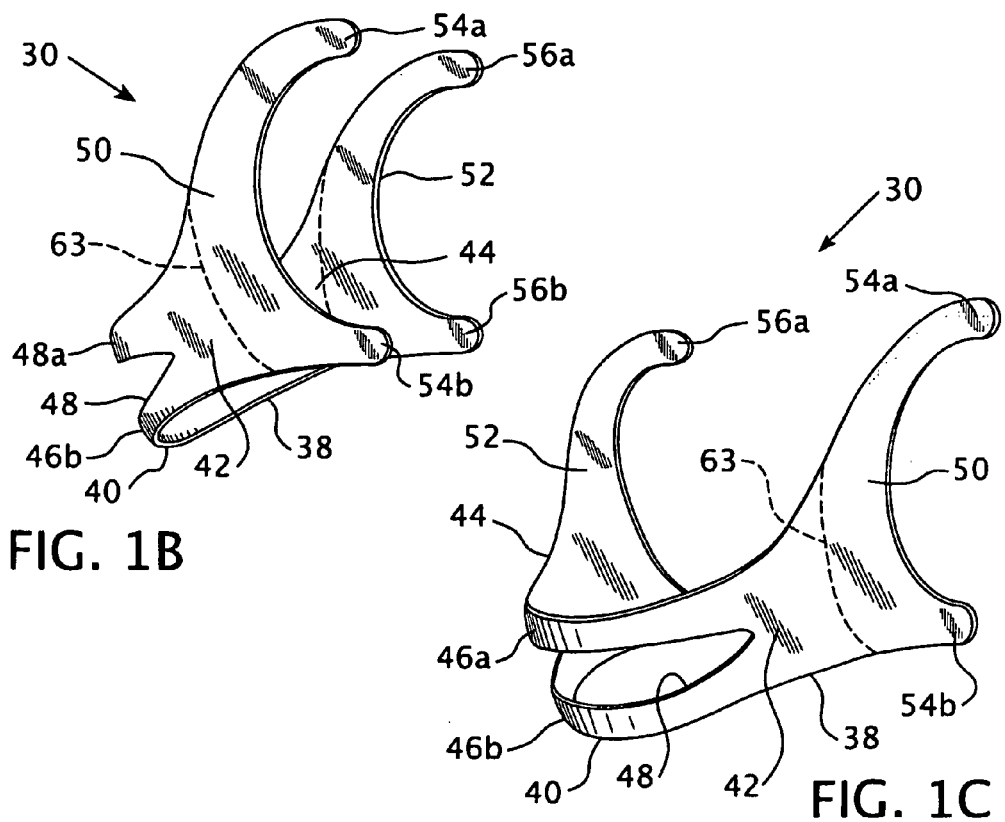

HEADGEAR AND INTERFACE ASSEMBLY USING SAME

CROSS-REFERENCE TO RELATED APPLICATIONS

This application claims priority under 35 U.S.C. § 119(e) from provisional U.S. patent application No. 60/527,235 filed Dec. 5, 2003 the contents of which are incorporated herein by reference.

BACKGROUND OF THE INVENTION

1. Field of the Invention

The present invention generally relates to a headgear adapted to support an object on the head of a user, and, more particularly, to a headgear having a beam that spans the nape of a patient's neck or back of the head for attaching an object to a patient while minimizing the amount of structure that overlies the user's hair, and to an interface assembly and pressure support system that includes such a headgear.

2. Description of the Related Art

There are numerous situations where it is necessary to couple an object to the face of a user. For example, non-invasive ventilation and pressure support therapies involve the placement of a patient interface device, which is typically a nasal mask that covers the nose, a nasal/oral mask that covers the nose and mouth, or full face mask that covers the patient face, on the face of a patient. The patient interface device interfaces the ventilator or pressure support device with the airway of the patient, so that a flow of breathing gas can be delivered from the pressure/flow generating device to the airway of the patient. Typically, non-invasive ventilation involves providing ventilatory gas to the airway of a patient without intubating the patient or surgically inserting a tracheal tube in their esophagus. Pressure support therapies involve providing a pressure, such as a continuous positive airway pressure (CPAP) or variable airway pressure, which varies with the patient's respiratory cycle (bi-level pressure support) or with the condition of the patient (auto-titrating pressure support), to treat a medical disorder, such as sleep apnea syndrome, in particular, obstructive sleep apnea (OSA), or congestive heart failure.

It is known to maintain such masks on the face of a wearer by a headgear having upper and lower straps, each having opposite ends threaded through connecting elements provided on the opposite sides and top of a mask. Because such masks are typically worn for an extended period of time, it is important the headgear maintain the mask in a tight enough seal against a patient's face without discomfort.

One such headgear is disclosed in U.S. Pat. No. 5,517,986 ("the '986 patent"), which is assigned to Respironics, Inc. of Pittsburgh, Pa., the assignee of the present application. The headgear taught by the '986 patent includes a cap-like headpiece adapted to fit the crown and back of a patient's head. Lower straps provide a two-point connection with a gas delivery mask. Straps depending from the headpiece are connected to and moveable relative to the lower straps. Additionally, a pair of upper straps can be used to provide a four-point connection with the gas delivery mask if needed.

Another such headgear also manufactured by Respironics, Inc. includes five straps extending in a star-like manner from a rear joining piece, which is positionable along the rear portion of a patient's head. The three uppermost straps are adapted to fit on the patient's head. A center top strap extends from the joining piece across the top of the patient's head to the patient's forehead. Upper side straps, which are provided on either side of the top strap, extend from the joining piece along the sides of a patient's head above the ears to attach to the top strap at the patient's forehead. The top strap includes a pair of elongated openings through which the upper side straps are threaded.

All of the straps in the headgear taught by the '986 patent include two components of a hook and loop fastener, such as VELCRO®. The exterior of the straps include a loop fastener portion, and a hook fastener tab portion is attached to the end of each strap. When securing or fastening, the end of each the upper side strap is bent back on itself to adhere the hook fastener tab portion to the exterior of the straps including the loop fastener portion. More specifically, the hook fastener tab portion of the top strap is adapted to be threaded through a connecting element of the gas delivery mask and then bent back on itself to adhere the hook fastener tab portion to the exterior loop fastener portion.

Yet another headgear is disclosed in U.S. Pat. No. 5,724,965, which is also assigned to Respironics, Inc. of Pittsburgh, Pa., the assignee of the present application. The headgear of U.S. Pat. No. 5,724,965 includes a load bearing ear piece that encircles each ear of the user. Two head bands connect the ear pieces to one another. One headband extends behind the head, and the other headband extends over the head.

These and other conventional headgear provide a convenient attachment of the patient interface device to the user's head. However, they suffer from several disadvantages. For example, conventional headgear straps cover significant portions of the user's head, including his or her hair. The present inventors recognized that some users prefer to avoid significant contact between their hair and the headgear. Contact between the headgear straps and the user's hair, for example, can result in entanglement of the straps with the hair, making the headgear difficult, and perhaps painful to remove. Thus, some users prefer that the headgear straps not cross over the hair. Therefore, a need exists for a headgear that is easy to use and adjust, is comfortable, provides a stable support for the object being attached to the user, and does not rest significantly on his or her hair.

In addition, some conventional headgear are perceived as bulky or cumbersome in that they cover a substantial area of the user's head. Furthermore, some users have an aversion to the relatively unattractive appearance of conventional headgear, and may prefer headgear that look less like a medical apparatus. Therefore, a need exists for a headgear that does not cover much of the patient's head so that it is perceived as being lightweight and slim and that appears less like a medical device. Because conventional headgear are soft, floppy, and typically have a myriad of flexible straps, the straps and other portions of the mask can become entangled. Therefore, a further need exists for a headgear that is easier to use in that it is less likely to become tangled in itself.

SUMMARY OF THE INVENTION

Accordingly, it is an object of the present invention to provide a headgear that overcomes the shortcomings of conventional headgear. This object is achieved according to one embodiment of the present invention by providing a headgear for attaching an object to a head of a user that includes a beam having a central portion, a first end portion, and a second end portion. The beam provides all of the force needed to secure such an object to a head of a user. The central portion wraps around a back of the neck or head and remains below the external occipital protuberance such that the first end portion is located proximate to the right side of the head and the second end portion is located proximate to the left side of the head. A first ear loop is coupled to the first end portion of the beam, and a second ear loop is coupled to the second end portion of the beam. The first ear loop includes a first upper arm adapted to be positioned above an ear, a first lower arm adapted to be positioned below the ear, or both. A second ear loop includes a second upper arm adapted to be positioned above the ear, a second lower arm adapted to be positioned below the user's ear, or both.

By providing a headgear that is disposed across the back of the head or neck, the headgear of the present invention avoids placing the straps over much of the patient's hair. The use of a beam with ear loops attached thereto that provide attachment points at both ears provides a relatively stable platform for supporting virtually any object on a patient's face. The present invention further provides a headgear that is comfortable to the patient, fits a wide range of head sizes, and provides improved aesthetics and usability.

It is yet another object of the present invention to provide an interface assembly and a system for delivering a breathing gas to a patient that uses the headgear of the present invention.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an" and "the" include plural referents unless the context clearly dictates otherwise.

BRIEF DESCRIPTION OF THE DRAWINGS

FIGS. 1A-1C are front, side, and rear perspective views of a first embodiment of a headgear according to the principles of the present invention;

DETAILED DESCRIPTION OF THE PRESENTLY PREFERRED EMBODIMENTS OF THE INVENTION

Figure 2:
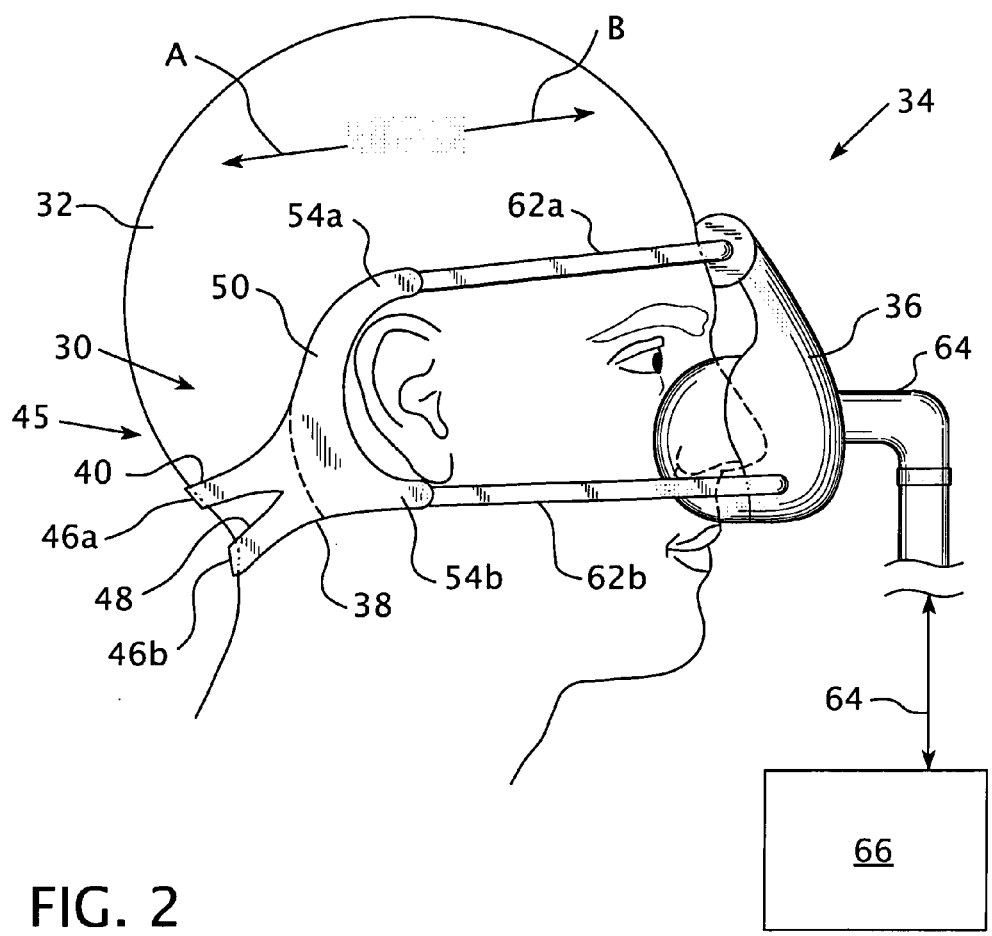
FIG. 2 is a side view of a patient wearing a first embodiment of an interface assembly including a mask and the headgear of FIGS. 1A-1C.

FIGS. 1A-1C schematically illustrate an exemplary embodiment of a portion of a headgear 30 according to the principles of the present invention, and FIG. 2 illustrates a patient 32 wearing an interface assembly, generally indicated at 34, including a mask 36 and headgear 30. Headgear 30 includes a beam 38, that is preferably rigid or semi-rigid, having a central portion 40, a first end portion 42, and a second end portion 44. Central portion 40 wraps around a back of a user's neck or head and remains below the user's external occipital protuberance, which is generally indicated at 45 and is typically located at the back of the skull near the bottom where the head meets the neck. When properly positioned on the patient, as shown in FIG. 2 for example, first end portion 42 of beam 38 is located proximate to the right side the patient's head and second end portion 44 is located proximate to the left side of the head. By providing a beam that terminates behind the user's ear, the headgear distributes the holding force on the nape of the neck.

Beam 38 provides a first force, generally indicated by arrow A, that urges the patient interface device 36 against the user's face. First force A represents all of the force needed to secure an object, such as mask 36, on the head of the user, and counterbalances a second force, as generally indicated by arrow B, which represents the pulling force of the patient interface device on the user. At all times during use of the interface assembly of the present invention, all portions of the beam 38 that provide first force A, which resists or counterbalances second force B, remains below the user's external occipital protuberance, so that no portions of the beam are above the user's external occipital protuberance during normal use of the headgear.

This configuration for the present invention provides two advantages. First, it allows the headgear to securely attach an object of the face of the user without the need for a strap above the external occipital protuberance. This minimizes the area where the headgear overlaps the user's hair. Second, this configuration allows forces A and B to be effectively directed through the user's ear, without having any portion of the headgear overlie the ear, which tends to be quite uncomfortable. Directing the interface securing force through the user's ear provides the most direct path for attaching an object on the face of the user.

Beam 38 can have a variety of shapes, sizes, and configurations so long as it provides the desired load supporting function and is comfortable for the patient and remains below the user's external occipital protuberance at all times during use of the headgear. For example, in the embodiment shown in FIGS. 1A-2, beam 38 is defined by a pair of beam members 46a and 46b separated by a gap 48. Beam members 46a and 46b define lower upper and lower portions of the beam, respectively, and join one another at the first end portion and the second end portion of the beam. This multi-beam configuration is advantageous in that it distributes the load supported by the beam over a relatively large area at the nape of the neck. However, a single beam member configuration is also contemplated by the present invention, as shown, for example, in FIGS. 5A and 5B. Of course, beam members in excess of two are also contemplated by the present invention.

The overall height of beam 38 is large enough to distribute the load over an area that is large enough to provide a comfortable load on the patient, yet small enough so as not to significantly impede the user's ability to articulate his or her head. The present invention also contemplates that the interior surface of beam 38, the overall shape of the beam, or a combination thereof can be contoured so as to more closely correspond to the surface of the patient or to correspond to the underlying bone structure, thereby maximizing patient comfort.

A first ear loop 50 is coupled to first end portion 42 of beam 38, and a second ear loop 52 is coupled to second end portion 44 of the beam. The first and second ear loops are preferably joined to the beam in a fixed relation, i.e., so that either ear loop does not move relative to the end portion of the beam to which it is attached. First ear loop 50 includes a first upper arm 54a that is positioned above an ear of a user when the headgear is properly located on the user, and a first lower arm 54b that is positioned below the user's ear. Similarly, second ear loop 52 includes a second upper arm 56a that is positioned above the ear of the user, and a second lower arm 56b that is positioned below the ear. The upper and lower arms on each ear loop provide mountings to which headgear straps or other suitable connecting elements are attached for securing an object to be affixed to a patient's face to headgear 30.

First and second ear loops 50 and 52 can have a variety of shapes, sizes, and configurations. In a presently preferred exemplary embodiment of the invention, the first and second ear loops are semi-circular and are integrally formed with the beam so that the combination of the ear loops and the beam define a unitary structure. The semi-circular or crescent shape provides a stable support on the side of the head and provides an area that is sized and shaped so as to receive the user's ear, as shown in FIG. 2. Upper and lower arms 54a, 54b, 56a, and 56b are also preferably integral with the first and second ear loops. The overall size of the ear loops and arms should be large enough to achieve the desired support and mounting functions, yet small enough to minimize the area of contact on the user's head. The present invention also contemplates that the interior surface of first and second ear loops 50 and 52 and upper and lower arms 54a, 54b, 56a, and 56b, the overall shape of these items, or a combination thereof can be contoured so as to more closely correspond to the surface of the patient or to correspond to the underlying bone structure, thereby maximizing patient comfort.

Beam 38, first and second ear loops 50 and 52, and upper and lower arms 54a, 54b, 56a, and 56b in this first exemplary embodiment are preferably formed so that the overall structure is rigid or semi-rigid. For present purposes, "semi-rigid" means that these structures retain their shape when no load is applied on them, but flex to some degree to allow them to conform to the patient to reduce pressure points when a load is applied.

Figure 3:
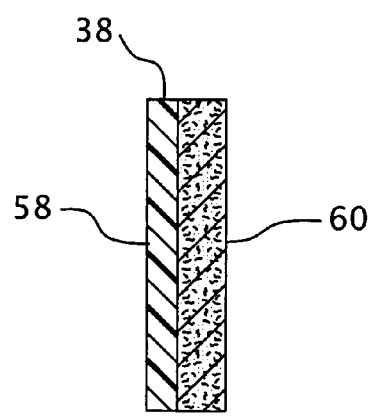
FIG. 3 is a cross-sectional view of a portion of the headgear of FIGS. 1A-1C taken along line 3-3 in FIG. 1A.

In an exemplary embodiment of the present invention, forming the beam, first and second ear loops, and upper and lower arms as a rigid or semi-rigid structure is accomplished by forming one or more of these structures from a support member 58 that is rigid or semi-rigid and providing a cushion member 60 disposed on a user contacting side of the support member. See FIG. 3. Examples of suitable rigid or semi-rigid materials suitable for use as support member 58 include metals (preferably a light-weight metal), plastics, or laminated fibers, or any combination thereof, such as a plastic reinforced with metal supports. Examples of materials suitable for use as cushion member 60 include, foam, cloth, silicon, rubber, or any combination thereof. The present invention also contemplates that the rigid or semi-rigid nature of the beam, first and second ear loops, and upper and lower arms can be accomplished in any conventional manner, such as by providing stiffened fabric. Stiffening the fabric can be accomplished, for example, by providing a rigid or semi-rigid support or batten in the fabric and/or coating, laminating, or otherwise reinforcing the fabric with a stiffening agent, such as through screen printing process.

The support member and the cushion material are joined in any conventional manner, such as by adhering the cushion to the support member. It is to be understood that the present invention contemplates selectively attaching the support member and the cushion material so that they can be detached from one another as needed. This is desirable, for example, for cleaning purposes. It also allows customization of the headgear by allowing the user to mix and match the cushion material and the support member. The present invention also contemplates that other structures can be provided on support member 58 and/or cushion member 60. For example, a protective covering (not shown) can be provided on either of these items.

An alternative embodiment of the present invention contemplates that first and second ear loops 50 and 52 are formed as rigid or semi-rigid structures and that beam 38 is not. This embodiment contemplates that the beam is a flexible member, such as piece of fabric material, that secures the first and second ear loops to one another. Dashed line 63 in FIGS. 1A-1C illustrate one possible point of delineation between the rigid or semi-rigid first and second ear loops and the beam portion of the headgear, which can be rigid, semi-rigid, or completely flexible.

As noted above, upper and lower arms 54a, 54b, 56a, and 56b of first and second ear loops 50 and 52 define a mounting member to which additional structures, such as straps, attach. These additional structures are needed to attach an object on a face of a user using headgear 30. In an exemplary embodiment of the present invention, these additional structures are flexible straps that connect to the object to be attached on the patient. More specifically, the present invention contemplates providing a first upper strap portion 62a coupled to first upper arm 54a and a first lower strap portion 62b coupled to first lower arm 54b. Similar straps can be coupled to second upper and lower arms 56a and 56b associated with second ear loop 52. The user interface device to be attached to the user, such as the mask, headgear 30, and the connecting straps define the interface assembly.

As shown in FIG. 2, straps 62a and 62b and the straps on the other side of the headgear (not shown) connect to various locations on mask 36 to hold the mask on the user's face. It can be appreciated that the connecting straps can attach to the user interface device in any one of an almost infinite number of configurations. Preferably, they are located so as to provide a secure attachment to the interface device and a stable support for this device on the user, while also maximizing patient comfort, for example, by avoiding overlapping sensitive areas such as the ears or eyes.

The straps connected to headgear 30 can be formed from a variety of materials, or combination of materials, and can have a variety of shapes, sizes, mechanical properties, and configurations. For example, the present invention contemplates that the straps are formed from a soft material (at least on the patient contacting side) and that the straps are slightly flexible. The present invention also contemplates that the attachment point for the straps on the upper and/or lower arms and the attachment points on the interface device can be fixed or adjustable, and can be selectively detachable. For example, the straps can be rotatably attached to headgear 30, the interface device (such as mask 36), or both. In addition, the straps can be connected to the headgear, interface device, or both via a snap so that the straps can be detached and reattached from headgear 30 or the interface device at the user's convenience.

In an exemplary embodiment of the present invention, the interface assembly includes headgear 30, the straps, and an interface device that couples a gas delivery conduit 64, typically referred to as a patient circuit, to an airway of the patient. Patient circuit 64 is typically a flexible tube that includes an attachment where it joins patient interface device 36. It should be noted that patient interface device 36 can be any conventional patient interface device, including a nasal mask, oral mask, nasal/oral mask, full face mask, nasal cannula, or any other device that interfaces with an airway of a patient. As schematically illustrated in FIG. 2, patient circuit 64 communicates a flow of gas from a gas flow generating device 66, such as a conventional pressure support system or ventilator, so that gas is delivered from the gas flow generator to the airway of the patient.

Gas flow generating device 66 can be any conventional device that accomplishes this function, such as a CPAP device, bi-level device, auto-titrating device, or any other pressure support system or ventilator using any conventional mode of therapy delivery. Although patient circuit 64 is illustrated in FIG. 2 as being a single limb circuit, the present invention contemplates that the patient circuit can include multiple limbs and can include other elements, such as filters, exhaust ports, flow control valve, pressure relief valves, humidifiers, and sensors.

Figure 4:
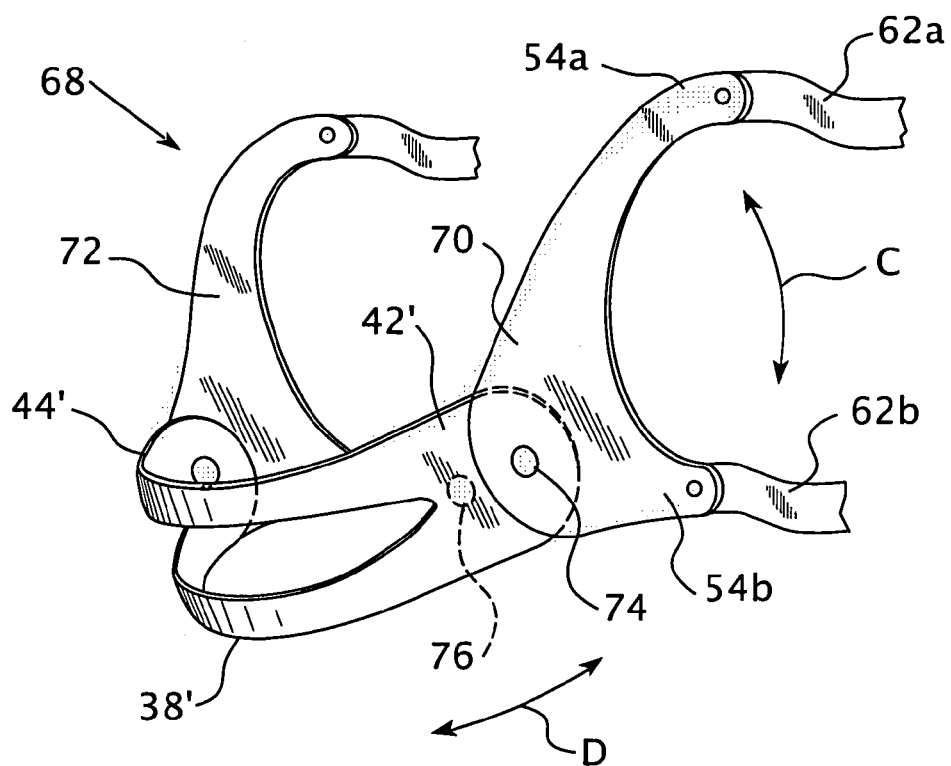
FIG. 4 is a rear perspective view of a second embodiment of a headgear according to the principles of the present invention.

FIG. 4 illustrates a headgear 68 according to a second embodiment of the present invention. Headgear 68 is similar to headgear 30 in many respects. However, headgear 68 illustrates several optional features that are believed to make the headgear easier to use and more comfortable for a wider variety differently sized and shaped patients.

For example, headgear 68 includes a first ear loop 70 and a second ear loop 72 that are rotatably coupled to first end portion 42' and second end portion 44', respectively, of beam 38'. This rotatable attachment can be provided in any one of a variety of techniques. In the illustrated exemplary embodiment, an axis 74 is provided on each end portion of the beam about which the ear loop rotates, as indicated, for example, by arrow C. Other techniques for allowing the ear loop to move relative to the beam include a sliding channel configuration, where the ear loop slides along a path relative to the beam by providing, for example, a tongue and groove or slot and pin, configuration that allows the ear loop to move relative to the beam, yet remain attached thereto. By allowing the ear loops to rotate relative to the beam, the headgear is able to self-align to a proper position on the patient so that one headgear size or style will fit a larger number of patients with the same degree of comfort that would otherwise require multiple headgear choices.

Another feature of headgear 68 is the ability to adjust the distance between first ear loop 70 and second ear loop 72 along a length of beam 38'. That is an adjusting mechanism associated with the first ear loop, the second ear loop or both is provided so that the first or second ear loops can be moved along the beam, as indicated, for example, by arrow D in FIG. 4. In this illustrated exemplary embodiment, this transverse adjustability made possible by providing an alternative axis 76 or mounting member to which the ear loop can selectively attach. To adjust the ear loops in the transverse direction (corresponding to arrow D) thereby effectively changing the length of beam 38, the first and/or second ear loop is detached from one axis and reattached to the other axis. This configuration provides flexibility in the size and configuration for the headgear.

Figure 5A:
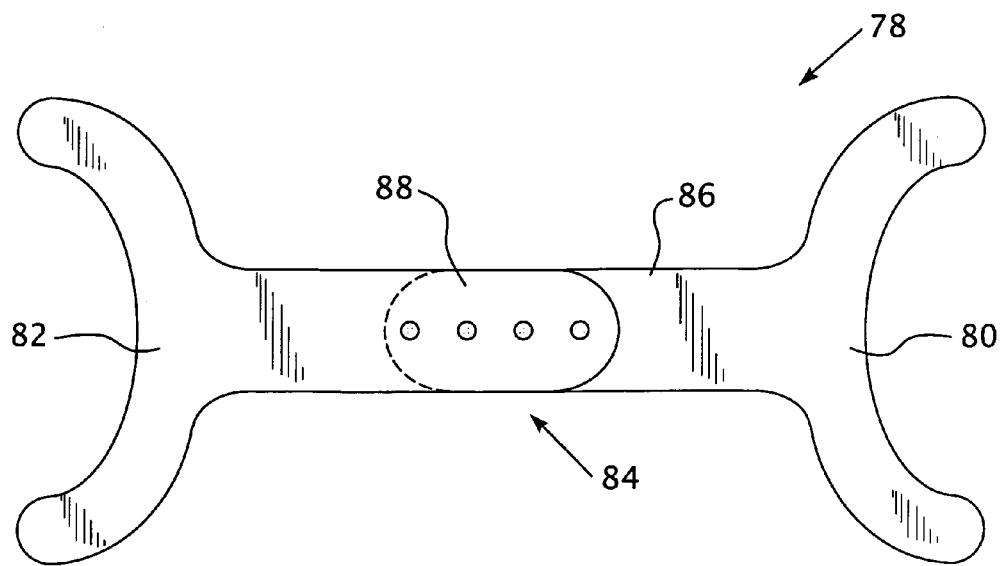
FIGS. 5A and 5B are front and side perspective views of a third embodiment of a headgear according to the principles of the present invention.
Figure 5B:
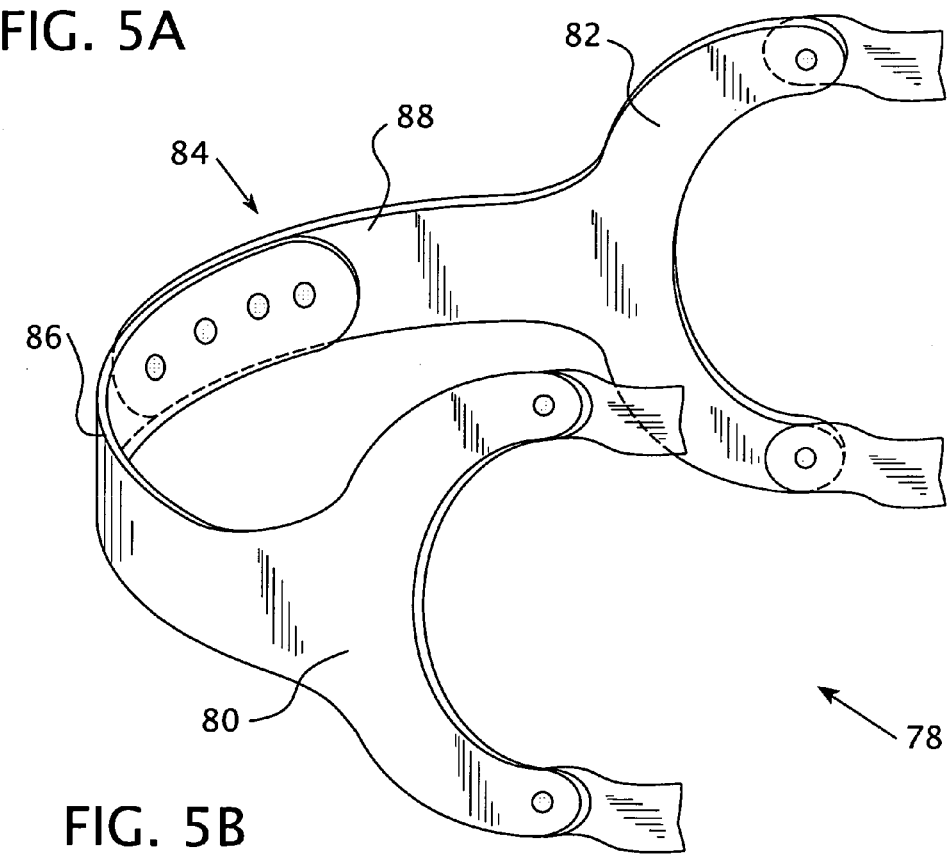

FIGS. 5A and 5B illustrate a headgear 78 that includes yet another technique for adjusting the distance between a first ear loop 80 and a second ear loop 82. In this embodiment, headgear 78 includes a beam, generally indicated at 84, that has a length adjusting capability rather than adjusting the attachment location for the ear loops. Of course, the present invention contemplates providing the beam length adjustment capability in combination with the ear loop position adjustment capability. Other than providing a length adjustment capability, beam 84 corresponds to beam 38, 38' from the previous embodiments.

Adjusting the length of beam 84 is made possible, according to one exemplary embodiment of the present invention, by separating beam 84 into a first beam member 86 and a second beam member 88 that are selectively connectable to one another at a number of different overlapping positions. That is, the first beam member and the second beam member are connectable such that the degree of overlap of these two members can be changed, thereby effectively changing the length of the beam. In this embodiment, a plurality of engaging portions or protrusions are provided on one beam member and a plurality of receiving portions are provided on the other beam member. The length of the beam is controlled based on the selection of which engaging portions are coupled to associated receiving portions. It is to be understood that this specific implementation represents only one of a variety of techniques that can be used to change the amount of overlap between the two beam members.

Figure 6:
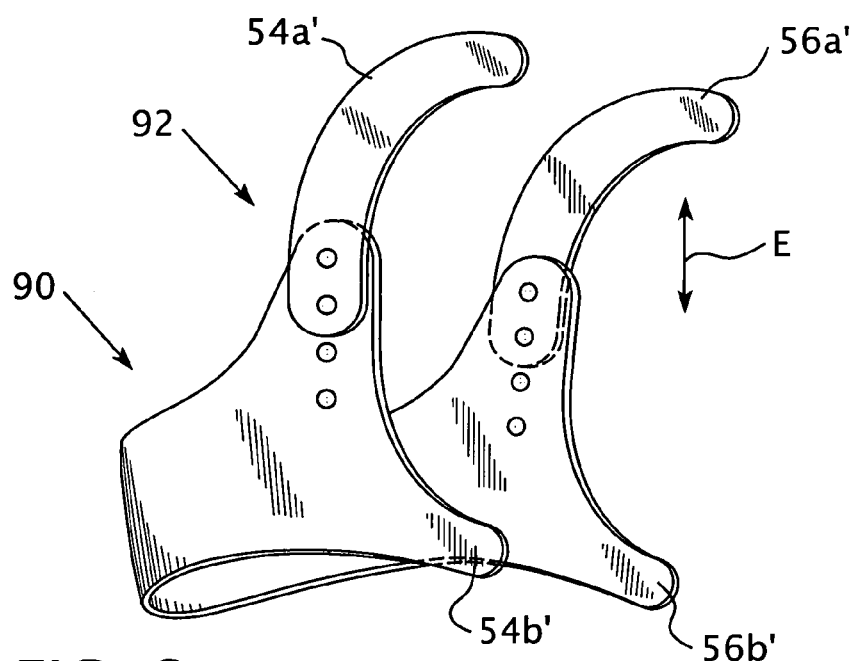
FIG. 6 is a front perspective view of a fourth embodiment of a headgear according to the principles of the present invention.

FIG. 6 is a front perspective view of a fourth embodiment of a headgear 90 according to the principles of the present invention. This embodiment is similar to the previous embodiments except that upper and lower arms 54a' and 54b' of first ear loop 50' and upper and lower arms 56a' and 56b' of second ear loop 52' are adjustable. That is, the distance between upper arms 54a', 56a' and lower arms 54b' and 56b' associated with each ear loop can be changed, as indicated by arrow E. This feature of the present invention allows the headgear to be customized to the physical dimensions of the patient.

In the illustrated exemplary embodiment, an adjusting mechanism 92 that allows the distance between the upper arms and the lower arms to be changed is similar to that discussed above with respect to FIGS. 5A and 5B. For example, in this embodiment, engaging portions or protrusions are provided on upper arms 54a', 56a' and corresponding receiving portions are provided on lower arms 54b' and 56b', or vice versa. It to be understood, however, that the present invention contemplates that any technique that allows the distance between the upper arms and the lower arms to be changed can be used.

Figure 7:
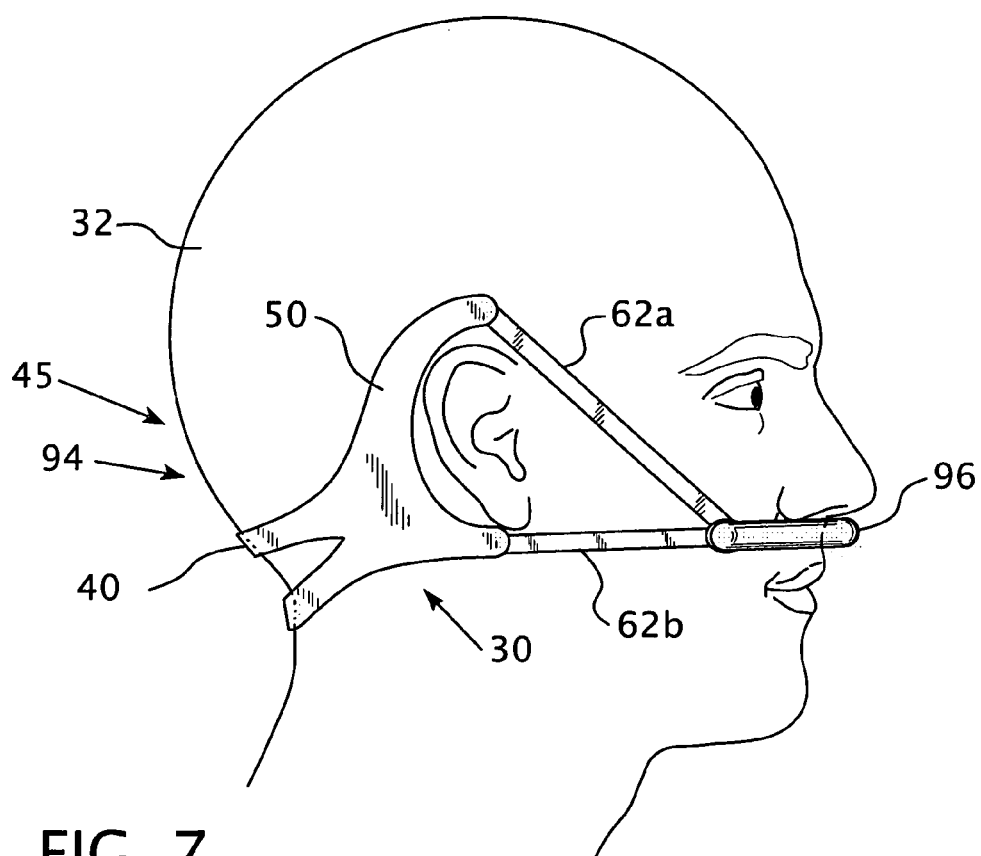
FIG. 7 is a side view of a patient wearing a second embodiment of an interface assembly including a patient monitoring device and the headgear of FIGS. 1A-1C.

FIG. 7 is a side view of a patient 32 wearing a second embodiment of an interface assembly 94 according to the principles of the present invention. In this embodiment, interface assembly includes headgear 30 described above with respect to FIGS. 1A-1C. However, the interface device for use with headgear 30 is not a nasal mask. Instead, the interface device is a patient monitoring device 96 that is attached to the face of the patient so as to monitor a parameter of the patient, such as patient airflow.

It is to be understood that the number, type, size, function, and other characteristics of the objects that can be used as the patient interface device that are suitable for use with a headgear of the present invention are nearly limitless. For example, the present invention contemplates that the headgear of the present invention can be used to attach other medical devices to the patient, such as a spirometer or other monitor, to the patient. On the other hand, the headgear can also be used to attach non-medical devices to the face of the user, such as gas masks, cosmetic objects, electronic devices, or apparel. No attempt is made in this disclosure to list the different types of objects that can serve as interface devices that can be held on the head of the patient by the headgear of the present invention. The monitoring device and headgear arrangement shown in FIG. 6 are provided merely as an example of other configurations for the interface device that are suitable for use therewith.

Figure 8:
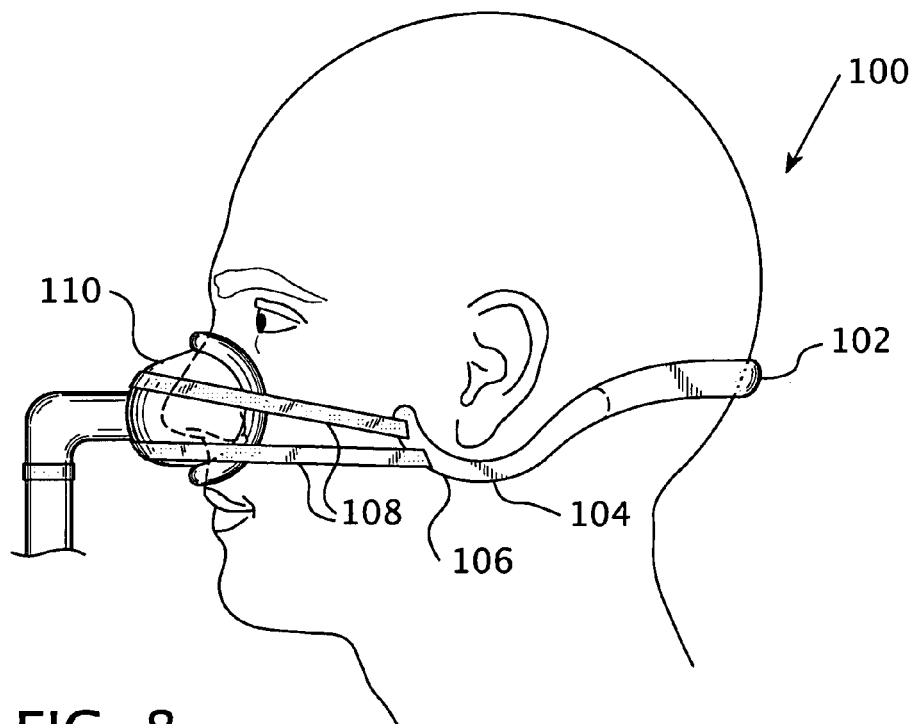
FIG. 8 is a side view of a patient wearing an interface assembly including a fifth embodiment of the headgear of the present invention.

FIG. 8 illustrates a fifth embodiment of a headgear 100 according to the principles of the present invention. In this embodiment, headgear 100 includes a beam 102 and first and second ear loops 104 (only one of which is shown). The nature, structure, and possible configurations for the beam and the ear loops in this embodiment and the interconnection between these members corresponds to that discussed above. For example, an exemplary embodiment of the present invention contemplates forming the ear loops as a rigid or semi-rigid structure and the beam as a rigid, semi-rigid, or flexible structure attached in a fixed relation to the ear loops. In this embodiment, the ear loop includes only a lower arm 106, so that no structure is located above the user's ear. Straps 108 attach the object to be held on the patient's face, such as a mask 110, to the ear loop portions of headgear 100.

Figure 9:
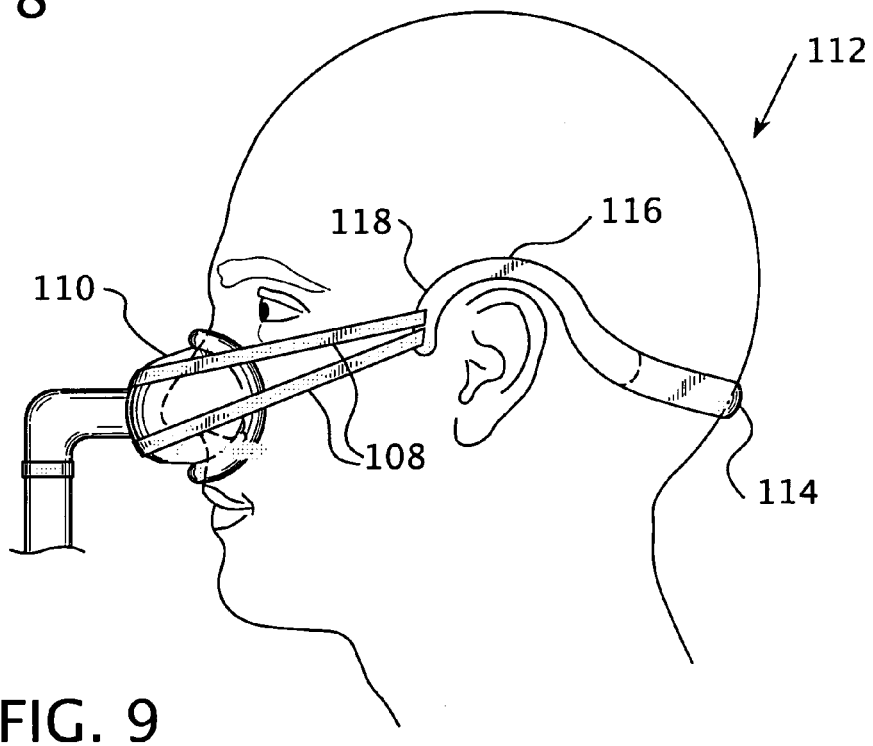
FIG. 9 is a side view of a patient wearing an interface assembly including a sixth embodiment of the headgear of the present invention.

FIG. 9 illustrates a sixth embodiment of a headgear 112 according to the principles of the present invention. In this embodiment, headgear 112 includes a beam 114 and first and second ear loops 116 (only one of which is shown). Again, the nature, structure, and possible configurations for the beam and the ear loops in this embodiment and the interconnection between these members corresponds to that discussed above. For example, an exemplary embodiment of the present invention contemplates forming the ear loops as a rigid or semi-rigid structure and the beam as a rigid, semi-rigid, or flexible structure attached in a fixed relation to the ear loops. In this embodiment, the ear loop includes only an upper arm 118, so that no structure is located above the user's ear. Straps 108 attach the object to be held on the patient's face, such as a mask 110, to the ear loop portions of headgear 112.

Figure 10:
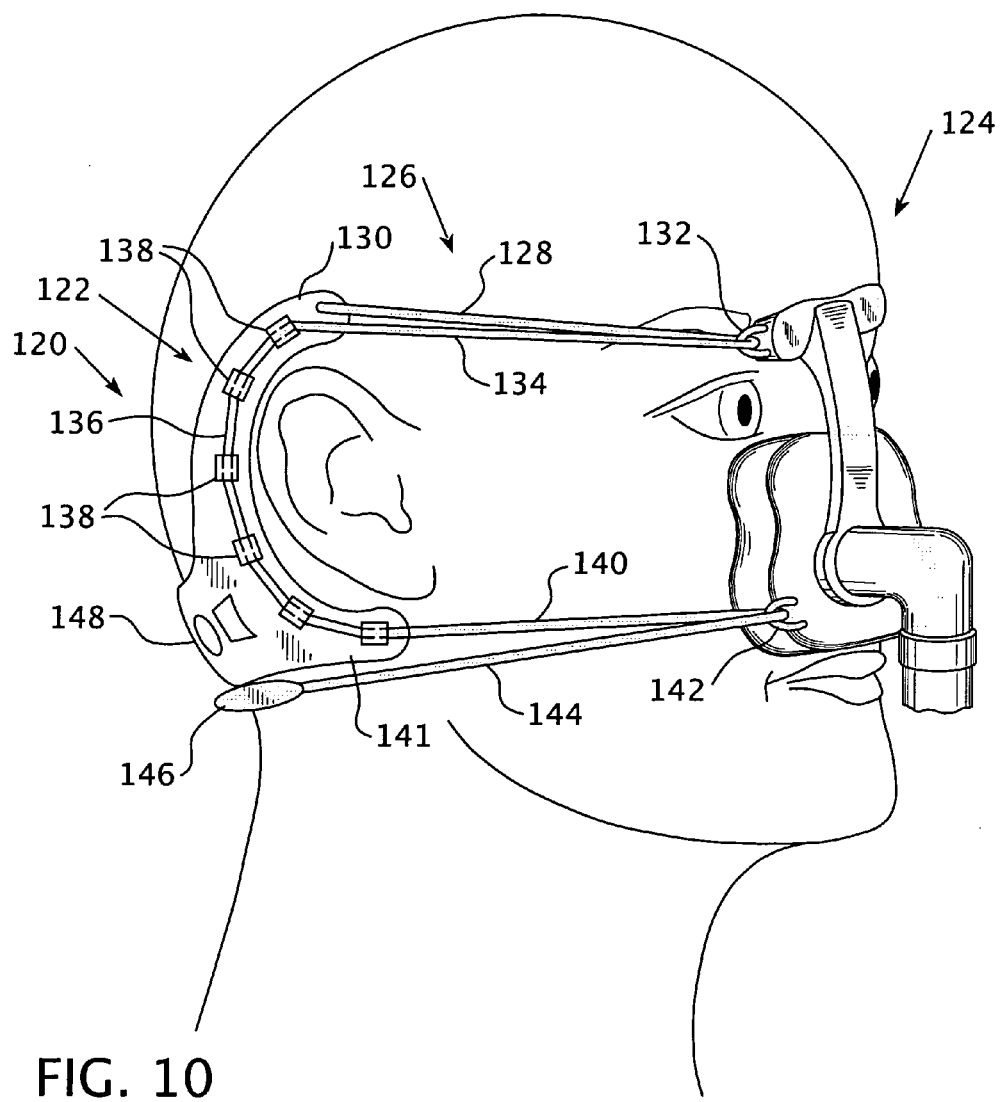
FIG. 10 is a front perspective views of a seventh embodiment of a headgear according to the principles of the present invention.

FIG. 10 is a side perspective view of a further embodiment of patient interface assembly 120 according to the principles of the present invention. The patient interface assembly includes a headgear 122, an object 124 to be attached to the user's face (which in this exemplary embodiment is a mask), and an attaching mechanism 126 for attaching object 124 to headgear 122. One of the unique aspects of this embodiment resides in this attaching mechanism. While FIG. 10 shows the attaching mechanism associated with one side of the headgear, it is to be understood that a similar attaching mechanism can be provided on the other side of the headgear.

Attaching mechanism 126 includes a single length of fastening material, such as a cord or strap, that is fed back and forth between headgear 122 and mask 124 through fastening elements on the mask and headgear. More specifically, in the illustrated exemplary embodiment, a first portion 128 of the fastening material is fixed to upper arm 130 and extends to a first portion of mask 124 where it is looped through a first fastening element 132 on the mask so that a second portion 134 extends back to the headgear. A third portion 136 of the fastening material is threaded through one or more guides 138 so that a fourth portion 140 extends from a lower arm 141 to the mask, is looped through a second fastening element 142 on the mask, and provides an attaching portion 144 that extends back to the headgear.

The fastening material is allowed to slide in first fastening element 132, guides 138, and second fastening element 142 so that increasing the tension on attaching portion 144 increases the tension on the mask at the first and the second fastening elements. This configuration allows the tension between the mask and the headgear to be effectively adjusted at two locations, i.e., the upper and lower arms, by pulling on one element, namely attaching portion 144. Once the desired tension is achieved, an attaching element 146 provided on attaching portion is secured to the headgear. For example, the present invention contemplates attaching portion 144 to headgear 120 by means of a hook and loop attachment device, where one element is provided on attaching element 146 and the other element is provided on beam 148. Of course, any conventional fastening technique can be used to secure the attaching portion of the attaching mechanism to the headgear.

It should be further understood that the present invention contemplates that the winding pattern by which the fastening material is attached to and between the headgear and the object to be attached to the patient can have a variety of different configurations. For example, more runs back and forth between the headgear and mask can be provided. The fastening material can cross between the sides of the patient interface assembly. The attaching portion can be attached to the mask. A single fastening material running between the sides of the mask can be provided, so that the user need only apply tension on one attaching portion to adjust the tension at multiple locations on the mask. The present invention contemplates, for example, eliminating first portion 128 of attaching element 146 so that the end of the attaching element is connected to the patient interface device rather than the headgear, as shown in FIG. 10. Thus, the first run for the attaching elements is attaching portion 134 running from the mask to the headgear.

It can be appreciated from the foregoing description that the present invention contemplates other shapes, sizes, and configurations for the interface assembly and, in particular, for the headgear and interface device defining the interface assembly. In addition, the straps or other connecting elements that are used to couple the headgear and interface device are also subject to variations. For example, straps need not be attached to both the upper and lower arms, but can be provided on either the upper arm or the lower arm depending on the specific arrangement needed to properly position the interface device on the head of the user.

By providing a headgear that is disposed across the back of the head or neck, the headgear of the present invention avoids placing the straps over much of the patient head and hair. The use of a beam with ear loops attached thereto that provide attachment points at both ears provides a relatively stable platform for supporting virtually any object on a patient's face. In addition, because the headgear does not cover much of the patient's head, it is perceived as being lightweight and slim and that appears less like a medical device, i.e., more aesthetically pleasing. In addition the use of the beam with ear loops provides a headgear that is less likely to become tangled in itself.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that, to the extent possible, the present invention contemplates that one or more features of any embodiment of the present invention can be combined with the features of any other embodiment.

What is claimed is:

1. A headgear for attaching an object to a head of a user comprising:
    a beam having a central portion, a first end portion, and a second end portion, wherein the central portion wraps around a back of a user's neck or head and remains below such a user's external occipital protuberance such that the first end portion is located proximate to a right side of such a user's head and the second end portion is located proximate to a left side of such a user's head, and wherein the beam is rigid or semi-rigid;
    a first ear loop operatively coupled to the first end portion of the beam, wherein the first ear loop is rigid or semi-rigid and is generally "C" shaped, wherein the first ear loop includes a first upper arm adapted to be positioned above an ear of such a user and a first lower arm adapted to be positioned below an ear of such a user, and wherein a first gap is defined between the first upper arm and the first lower arm such that the first ear loop is not disposed over a front of such a user's ear responsive to the headgear being donned by a user;
    a second ear loop operatively coupled to the second end portion of the beam, wherein the second ear loop is rigid or semi-rigid and is generally "C" shaped, wherein the second ear loop includes a second upper arm adapted to be positioned above an ear of such a user and a second lower arm adapted to be positioned below an ear of such a user, and wherein a second gap is defined between the second upper arm and the second lower arm such that the second ear loop is not disposed over a front of such a user's ear responsive to the headgear being donned by a user;
    a first strap operatively coupled to the first upper arm or the first lower arm of the first ear loop; and
    a second strap operatively coupled to the second upper arm or the second lower arm of the second ear loop, and wherein the headgear does not include a strap disposed over a top of such a user's head when the headgear is donned by a user.

2. The headgear of claim 1, wherein the first ear loop and the second ear loop are rotatably coupled to the beam.

3. The headgear of claim 1, wherein the beam includes an upper portion and a lower portion, and wherein the upper portion and the lower portion are joined at the first end portion and the second end portion and separated at the central portion.

4. The headgear of claim 1, wherein the first ear loop and the second ear loop are integral with the beam.

5. The headgear of claim 1, further comprising an adjusting mechanism associated with the beam adapted to adjust to adjust a distance between the first end portion and the second end portion.

6. The headgear of claim 1, further comprising an adjusting mechanism associated with at least one of the first ear loop and the second ear loop adapted to adjust a distance between the first ear loop and the second ear loop along a length of the beam.

7. The headgear of claim 1, wherein the first ear loop includes both the first upper arm and the first lower arm, and wherein the second ear loop includes both the second upper arm and the second lower arm.

8. The headgear of claim 1, wherein at least a portion of the beam, the first ear loop, the second ear loop, or any combination thereof comprises a cushioning member disposed on a rigid or semi-rigid support member.

9. The headgear of claim 7, wherein the first strap is coupled to the first upper arm and the second strap is coupled to the second upper arm, and further comprising:
    a third strap operatively coupled to the first lower arm; and
    a fourth strap operatively coupled to the second lower arm.

10. The headgear of claim 1, wherein the central portion has a curvature substantially corresponding to a curvature of a nape of human neck.

11. An interface assembly comprising:
    a) a user interface device adapted to contact a portion of a face of a user; and
    b) a headgear comprising:
        1) a beam having a central portion, a first end portion, and a second end portion, wherein the central portion wraps around such a user's neck or head and remains below such a user's external occipital protuberance such that the first end portion is located proximate to a right side of such a user's head and the second end portion is located proximate to a left side of such a user's head, and wherein the beam is rigid or semi-rigid,
        2) a first ear loop operatively coupled to the first end portion of the beam, wherein the first ear loop is rigid or semi-rigid and is generally "C" shaped, wherein the first ear loop includes a first upper arm adapted to be positioned above an ear of such a user and a first lower arm adapted to be positioned below an ear of such a user, and wherein a first gap is defined between the first upper arm and the first lower arm such that the first ear loop is not disposed over a front of such a user's ear responsive to the headgear being donned by a user,
        3) a second ear loop operatively coupled to the second end portion of the beam, wherein the second ear loop is rigid or semi-rigid and is generally "C" shaped, wherein the second ear loop includes a second upper arm adapted to be positioned above an ear of such a user and a second lower arm adapted to be positioned below an ear of such a user, and wherein a second gap is defined between the second upper arm and the second lower arm such that the second ear loop is not disposed over a front of such a user's ear responsive to the headgear being donned by a user,
        4) a first strap operatively coupling the first ear loop to a first portion of the user interface device, and
        5) a second strap operatively coupling the second ear loop to a second portion of the user interface device, and wherein the headgear does not include a strap disposed over a top of such a user's head when the headgear is donned by a user.

12. The interface assembly of claim 11, wherein the first ear loop and the second ear loop rotatably coupled to the beam.

13. The interface assembly of claim 11, wherein the beam includes an upper portion and a lower portion, and wherein the upper portion and the lower portion are joined at the first end portion and the second end portion and separated at the central portion.

14. The interface assembly of claim 11, wherein the first ear loop and the second ear loop are integral with the beam.

15. The interface assembly of claim 11, further comprising an adjusting mechanism associated with the beam adapted to adjust a distance between the first end portion and the second end portion 16. The interface assembly of claim 11, further comprising an adjusting mechanism associated with at least one of the first ear loop and the second ear loop adapted to adjust a distance between the first ear loop and the second ear loop along a length of the beam.

17. The interface assembly of claim 11, wherein the first ear loop includes both the first upper arm and the first lower arm, and wherein the second ear loop includes both the second upper arm and the second lower arm.

18. The interface assembly of claim 11, wherein at least a portion of the beam, the first ear loop, the second ear loop, or any combination thereof comprises a cushioning member disposed on a rigid or semi-rigid support member.

19. The interface assembly of claim 17, wherein the first strap is operatively coupled to the first upper arm, and the second strap is operatively coupled to the second upper arm, and further comprising:
a third strap operatively coupled to the first lower arm; and
a fourth strap operatively coupled to the second upper arm.

20. The interface assembly of claim 11, wherein the central portion has a curvature substantially corresponding to a curvature of a nape of human neck.

21. The interface assembly of claim 11, wherein the user interface device is a nasal mask, a nasal/oral mask, a full face mask, a respiratory monitor, or any combination thereof.

22. A system for delivering a breathing gas to a patient comprising:
a) a gas flow generating device that produces a flow of gas;
b) a conduit having a first end portion operatively coupled to the gas flow generating device and a second end portion, wherein the conduit carries the flow of gas from the gas flow generating device during operation of the system;
c) a user interface device coupled to the second end portion of the conduit; and
d) a headgear comprising:
1) a beam having a central portion, a first end portion, and a second end portion, wherein the central portion wraps around such a user's neck and remains below such a user's external occipital protuberance such that the first end portion is located proximate to a right side of such a user's head and the second end portion is located proximate to a left side of such a user's head, and wherein the beam is rigid or semi-rigid,
2) a first ear loop operatively coupled to the first end portion of the beam, wherein the first ear loop is rigid or semi-rigid and is generally "C" shaped, wherein the first ear loop includes a first upper arm adapted to be positioned above an ear of such a user and a first lower arm adapted to be positioned below an ear of such a user, and wherein a first gap is defined between the first upper arm and the first lower arm such that the first ear loop is not disposed over a front of such a user's ear responsive to the headgear being donned by a user,
3) a second ear loop operatively coupled to the second end portion of the beam, wherein the second ear loop is rigid or semi-rigid and is generally "C" shaped, wherein the second ear loop includes a second upper arm adapted to be positioned above an ear of such a user and a second lower arm adapted to be positioned below an ear of such a user, and wherein a second gap is defined between the second upper arm and the second lower arm such that the second ear loop is not disposed over a front of such a user's ear responsive to the headgear being donned by a user,
4) a first strap operatively coupling the first ear loop to a first portion of the user interface device, and
5) a second strap operatively coupling the second ear loop to a second portion of the user interface device, and wherein the headgear does not include a strap disposed over a top of such a user's head when the headgear is donned by a user.

23. The system of claim 22, wherein the first ear loop and the second ear loop are rotatably coupled to the beam.

24. The system of claim 22, wherein the beam includes an upper portion and a lower portion, and wherein the upper portion and the lower portion are joined at the first end portion and the second end portion and separated at the central portion.

25. The system of claim 22, wherein the first ear loop and the second ear loop are integral with the beam.

26. The system of claim 22, further comprising an adjusting mechanism associated with the beam adapted to adjust a distance between the first end portion and the second end portion.

27. The system of claim 22, further comprising an adjusting mechanism associated with at least one of the first ear loop and the second ear loop adapted to adjust a distance between the first ear loop and the second ear loop along a length of the beam.

28. The system of claim 22, wherein the first ear loop includes both the first upper arm and the first lower arm, and wherein the second ear loop includes both the second upper arm and the second lower arm.

29. The system of claim 22, wherein at least a portion of the beam, the first ear loop, the second ear loop, or any combination thereof comprises a cushioning member disposed on a rigid or semi-rigid support member.

30. The system of claim 28, wherein the first strap is operatively coupled to the first upper arm, and the second strap is operatively coupled to the second upper arm, and further comprising:
a third strap operatively coupled to the first lower arm; and
a fourth strap operatively coupled to the second upper arm.

31. The system of claim 22, wherein the central portion has a curvature substantially corresponding to a curvature of a nape of human neck.

32. The system of claim 22, wherein the user interface device is a nasal mask, a nasal/oral mask, a full face mask, a respiratory monitor, or any combination thereof.

* * * * *